(12) United States Patent
Nishibayashi (10) Patent No.: US 6,497,668 B2
(45) Date of Patent: Dec. 24, 2002

(54) BLOOD-PRESSURE MEASURING APPARATUS

(75) Inventor: Hideo Nishibayashi, Komaki (JP)

(73) Assignee: Colin Corporation, Komaki (JP)

( * ) Notice: Subject to any disclaimer, the term of this patent is extended or adjusted under 35 U.S.C. 154(b) by 93 days.

(21) Appl. No.: 09/811,490

(22) Filed: Mar. 20, 2001

(65) Prior Publication Data

US 2002/0002340 A1 Jan. 3, 2002

(30) Foreign Application Priority Data

May 29, 2000 (JP) ........................................ 2000-158629

(51) Int. Cl.$^7$ .............................................. A61B 05/00
(52) U.S. Cl. ........................................ 600/494; 600/495
(58) Field of Search .............................. 600/490, 493–6

(56) References Cited

U.S. PATENT DOCUMENTS

| | | | | |
|---|---|---|---|---|
| 4,850,368 A | * | 7/1989 | Miyawaki | 600/490 |
| 5,094,245 A | * | 3/1992 | Shirasaki | 600/496 |
| 5,423,324 A | * | 6/1995 | Tomita | 600/495 |
| 6,346,083 B1 | * | 2/2002 | Nishibayashi et al. | 600/490 |

* cited by examiner

*Primary Examiner*—Robert L. Nasser
(74) *Attorney, Agent, or Firm*—Oliff & Berridge, PLC (57) ABSTRACT

An apparatus for measuring a systolic blood pressure of a living subject, including an inflatable cuff which is adapted to be wound around a body portion of the subject and includes a first inflatable bag which is inflatable to press an artery of the body portion, a first amplitude determining device for determining a first amplitude of each of a plurality of heartbeat-synchronous pulses of a first pulse wave which is produced in the first inflatable bag when a pressure in the first bag is changed, a pulse-wave detecting device which detects a second pulse wave which propagates from the artery to a downstream-side portion of the cuff as seen in a blood-flow direction in which blood flows in the artery, a second amplitude determining device for determining a second amplitude of each of a plurality of heartbeat-synchronous pulses of the second pulse wave which is detected by the pulse-wave detecting device when the pressure of the first inflatable bag is changed, a ratio calculating device for calculating a ratio of one of each of the first amplitudes determined by the first amplitude determining means and each of the second amplitudes determined by the second amplitude determining means to the other of the each of the first amplitudes and the each of the second amplitudes, and a blood-pressure determining device for determining the systolic blood pressure of the subject, based on the ratios calculated by the ratio calculating device.

10 Claims, 6 Drawing Sheets

BLOOD-PRESSURE MEASURING APPARATUS

BACKGROUND OF THE INVENTION

1. Field of the Invention

The present invention relates to an oscillometric-type blood-pressure measuring apparatus which employs, for improving the accuracy of blood-pressure measurements, a pulse-wave detecting device for detecting a pulse wave propagated to a downstream-side portion of an inflatable cuff which is wound around a body portion of a living subject, and which determines a blood pressure of the subject based on the pulse wave detected by the pulse-wave detecting device. The downstream-side portion of the cuff means the portion thereof other than the upstream-side portion thereof.

2. Related Art Statement

Generally, an oscillometric-type blood-pressure (BP) measuring apparatus includes (a) an inflatable cuff which is adapted to be wound around a body portion of a living subject and includes an inflatable bag; (b) a pressure changing device which increases a pressing pressure of the inflatable bag up to a prescribed pressure value which can completely stop the flow of blood through an artery under the cuff, and subsequently slowly decreases the pressure in the bag at a prescribed rate; a pressure sensor which continuously detects the pressure in the bag during the slow deflation of the bag; a pulse-wave filter which extracts a pulse wave from the pressure in the bag, continuously detected by the pressure sensor; and a means for determining, as a systolic blood pressure of the subject, a pressure in the bag at a rising point where respective amplitudes of successive heartbeat-synchronous pulses of the extracted pulse wave significantly greatly changes to increase.

However, the above BP measuring apparatus has the problem that since the rising point of the amplitudes of the pulse wave is indefinite, the determined systolic BP value of the subject may be inaccurate. The reason is that even if the pressing pressure of the cuff is higher than the systolic BP value of the subject, the pulsation of the artery under the cuff may start under an upstream-side portion of the cuff. In particular, in the case where the body portion around which the cuff is wound is difficult to completely stop the flow of blood in the artery thereof, the pulsation of the artery is likely to be large even if the pressing pressure of the cuff may be higher than the systolic BP value of the subject. Therefore, the rising point of the amplitudes of the pulse wave is likely to be indefinite.

To solve the above-indicated problem, it has been proposed to provide a pulse-wave detecting device on an inner side and a downstream side of an inflatable bag of an inflatable cuff and determine a BP value of a living subject based on respective amplitudes of heartbeat-synchronous pulses of a pulse wave detected by the pulse-wave detecting device. For example, the pulse-wave detecting device may be one which includes another or second inflatable bag which is independent of the first inflatable bag for pressing the artery, and is provided on the downstream side of the first bag; and a pressure sensor which detects a pressure in the second bag. A BP value of the subject is determined based on respective amplitudes of heartbeat-synchronous pulses of a pulse wave which is produced in the second bag and is detected by the pressure sensor. Even if the pulsation of the artery may occur under the upstream-side portion of the cuff when the pressing pressure of the cuff is higher than the systolic BP value of the subject, the pulsation does not directly propagate to the second inflatable bag provided in the downstream-side portion of the cuff. Therefore, a definite rising point of the amplitudes of the pulse wave can be found and accordingly an accurate systolic BP value of the subject can be determined.

However, in some cases, the rising point of the amplitudes of the pulse wave detected by the above-described pulse-wave detecting device may be indefinite. In particular, in the case where a pulse wave is detected from an ankle of a living subject, the rising point is likely to be indefinite. The reason is that although the pulse wave which occurs under the upstream-side portion of the cuff when the pressure of the cuff is higher than the systolic BP value of the subject does not directly propagate to the second inflatable bag of the pulse-wave detecting device, the pulse wave is detected by the pulse-wave detecting device via the first inflatable bag. More specifically described, the pulse wave which occurs under the upstream-side portion of the cuff when the cuff pressure is higher than the systolic BP value, causes a pressure oscillation in the first inflatable bag, which in turn is detected by the pulse-wave detecting device. Therefore, the systolic BP value determined based on the amplitudes of the pulse wave detected by the pulse-wave detecting device may be inaccurate.

SUMMARY OF THE INVENTION

It is an object of the present invention to provide a blood-pressure measuring apparatus which can measure an accurate systolic blood pressure of a living subject.

The above object has been achieved by the present invention. According to a first feature of the present invention, there is provided an apparatus for measuring a systolic blood pressure of a living subject, comprising an inflatable cuff which is adapted to be wound around a body portion of the subject and includes a first inflatable bag which is inflatable to press an artery of the body portion; a first amplitude determining means for determining a first amplitude of each of a plurality of heartbeat-synchronous pulses of a first pulse wave which is produced in the first inflatable bag when a pressure in the first bag is changed; a pulse-wave detecting device which detects a second pulse wave which propagates from the artery to a downstream-side portion of the cuff as seen in a blood-flow direction in which blood flows in the artery; a second amplitude determining means for determining a second amplitude of each of a plurality of heartbeat-synchronous pulses of the second pulse wave which is detected by the pulse-wave detecting device when the pressure of the first inflatable bag is changed; a ratio calculating means for calculating a ratio of one of each of the first amplitudes determined by the first amplitude determining means and each of the second amplitudes determined by the second amplitude determining means to the other of said each of the first amplitudes and said each of the second amplitudes; and a blood-pressure determining means for determining the systolic blood pressure of the subject, based on the ratios calculated by the ratio calculating means.

In the present BP measuring apparatus, the first amplitude determining means determines a first amplitude of each of a plurality of heartbeat-synchronous pulses of a first pulse wave which is produced in the first inflatable bag when a pressure in the first bag is changed; the second amplitude determining means determines a second amplitude of each of a plurality of heartbeat-synchronous pulses of a second pulse wave which is detected by the pulse-wave detecting device when the pressure of the first inflatable bag is changed; the ratio calculating means calculates a ratio of one of each of the first amplitudes and each of the second amplitudes to the other of the each of the first amplitudes and the each of the second amplitudes; and the BP determining means determines, based on the ratios, the systolic BP value of the subject. When the pressure of the first inflatable bag is higher than the systolic BP value of the subject, the pulse-wave detecting device including the second inflatable bag provided on the downstream side of the first inflatable bag detects the pulse wave only indirectly via the first bag. Thus, the second amplitudes are small. On the other hand, when the pressure of the first bag is not higher than the systolic BP value of the subject, the pulse-wave detecting device detects the pulse wave not only indirectly via the first bag but also directly from the artery. Thus, the second amplitudes are great. However, even if the pressure of the first bag is higher than the systolic BP value, the pressure pulse wave is directly transmitted from the artery to the first bag. Thus, the first amplitudes do not change so greatly as the second amplitude, when the pressure of the first bag is equal to the systolic BP value. Therefore, the amplitude ratios calculated by the ratio calculating means greatly changes when the pressure of the first bag is equal to the systolic BP value, and the BP determining means can determine, based on the amplitude ratios, an accurate systolic BP value of the subject.

According to a second feature of the present invention, the pulse-wave detecting device includes a second inflatable bag which is provided in the downstream-side portion of the cuff wound around the body portion of the living subject, such that the second inflatable bag is located on a downstream side of a first portion of the first inflatable bag and on an inner side of a second portion of the first bag, the second bag having, in the blood-flow direction, a width smaller than a width of the first bag, and wherein the pulse-wave detecting device detects the second pulse wave which is produced in the second bag. Since the present BP measuring apparatus enjoys a simple construction, it can be produced with ease and at low cost.

According to a third feature of the present invention, the blood-pressure determining means determines the systolic blood pressure of the subject, based on the ratios which are calculated, by the ratio calculating means, based on a portion of pre-selected ones of the first amplitudes or the second amplitudes that falls within a predetermined pressure range. Since the BP determining means determines the systolic BP value of the subject, based on the ratios calculated based on only a portion of pre-selected ones of the first amplitudes or the second amplitudes that falls within a predetermined pressure range, the BP determining means does not erroneously determine a systolic BP value in a pressure range different from the predetermined pressure range. Thus, the BP determining means can obtain a more accurate systolic BP value of the subject.

According to a fourth feature of the present invention, the blood-pressure measuring apparatus further comprises a smoothing means for smoothing the ratios calculated by the ratio calculating means, and the blood-pressure determining means determines the systolic blood pressure of the subject, based on the ratios smoothed by the smoothing means. Even if the amplitude ratios calculated by the ratio calculating means may temporarily greatly change, the smoothing means smoothes or eliminates the temporary change of the amplitude ratios, and the BP determining means determines the systolic BP vale of the subject based on the smoothed amplitude ratios. Thus, the BP determining means can obtain a more accurate systolic BP value of the subject.

According to a fifth feature of the present invention, the smoothing means smoothes the ratios which are calculated, by the ratio calculating means, based on a portion of pre-selected ones of the first amplitudes or the second amplitudes that falls within a predetermined pressure range, and the blood-pressure determining means determines the systolic blood pressure of the subject, based on the ratios smoothed by the smoothing means. Since the BP determining means determines the systolic BP value of the subject, based on the ratios calculated based on only a portion of pre-selected ones of the first amplitudes or the second amplitudes that falls within a predetermined pressure range, the BP determining means does not erroneously determine a systolic BP value based on a great change of the amplitude ratios in a pressure range different from the predetermined pressure range. In addition, even if the amplitude ratios may temporarily greatly change in a pressure range different from the predetermined pressure range, the smoothing means smoothes or eliminates the temporary change of the amplitude ratios, and the BP determining means does not determine an erroneous systolic BP vale of the subject based on the temporary change of the amplitude ratios. Thus, the BP determining means can obtain a more accurate systolic BP value of the subject.

BRIEF DESCRIPTION OF THE DRAWINGS

The above and optional objects, features, and advantages of the present invention will be better understood by reading the following detailed description of preferred embodiments of the invention when considered in conjunction with the accompanying drawings, in which.

DETAILED DESCRIPTION OF PREFERRED EMBODIMENTS

Figure 1:
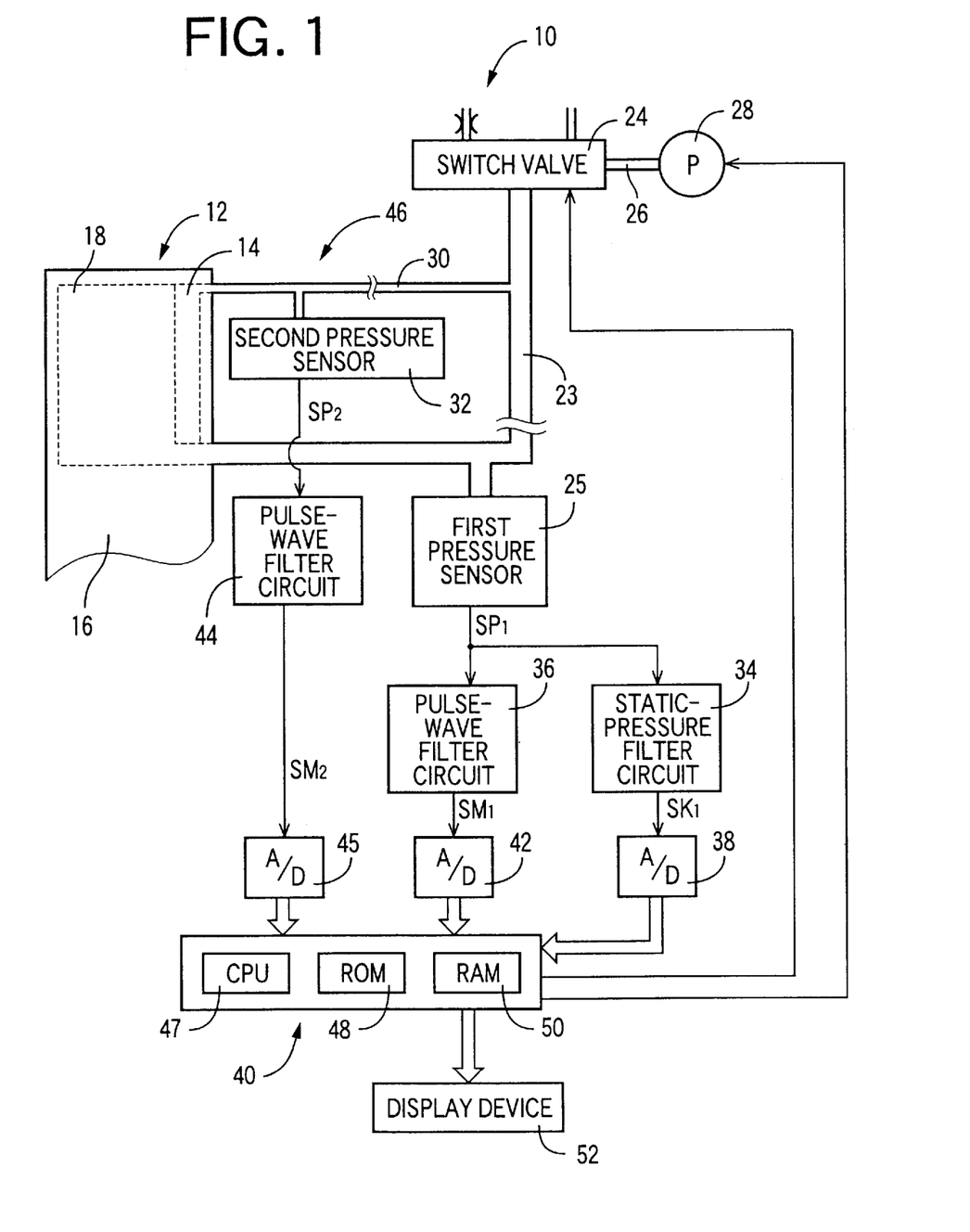
FIG. 1 is a diagrammatic view for explaining a construction of a blood-pressure (BP) measuring apparatus embodying the present invention.

Hereinafter, there will be described an embodiment of the present invention, by reference to the drawings. FIG. 1 is a diagrammatic view for explaining the construction of a blood-pressure (BP) measuring apparatus 10 to which the present invention is applied.

In FIG. 1, the BP measuring apparatus 10 includes an inflatable cuff 12 which is adapted to be wound around an ankle 19 of a living subject. The present cuff 12 differs from a cuff which is commonly used to measure a BP value from an ankle of a living subject, in that the cuff 12 has a second rubber bag 14 functioning as a second inflatable bag. More specifically described, the cuff 12 includes a belt-like bag 16 which is formed of a non-stretchable and considerably hard cloth and which has a shape that assures that the bag 16 is advantageously wound around an ankle of a living subject; and a first rubber bag 18 which has a prescribed width somewhat shorter than that of the belt-like bag 16, and a prescribed length shorter than a circumferential length of the ankle (e.g., the length of the first rubber bag 18 is equal to about two thirds of an average circumferential length of ankle). The first rubber bag 18 functions as a first inflatable bag, and is used mainly for pressing an artery 20 of the ankle 19 around which the cuff 12 is wound, and thereby occluding the artery, i.e., stopping the flow of blood in the artery.

The cuff 12 additionally includes, in a distal-side or downstream-side end of the belt-like bag 16, the second rubber bag 14 at a location inside a portion of the first rubber bag 18 and on a distal or downstream side of another portion of the same 18, in a state in which the cuff 12 is wound around the ankle 19. The second rubber bag 14 has a prescribed length substantially equal to that of the first rubber bag 18, and has a prescribed width not greater than one second of that of the same 18 (the width of the second bag 14 is equal to, e.g., one fourth to one sixth of the width of the first bag 18). The second rubber bag 13 is used mainly for detecting the pulsation of the artery 20 of the ankle 19 around which the cuff 12 is wound.

Figure 2:
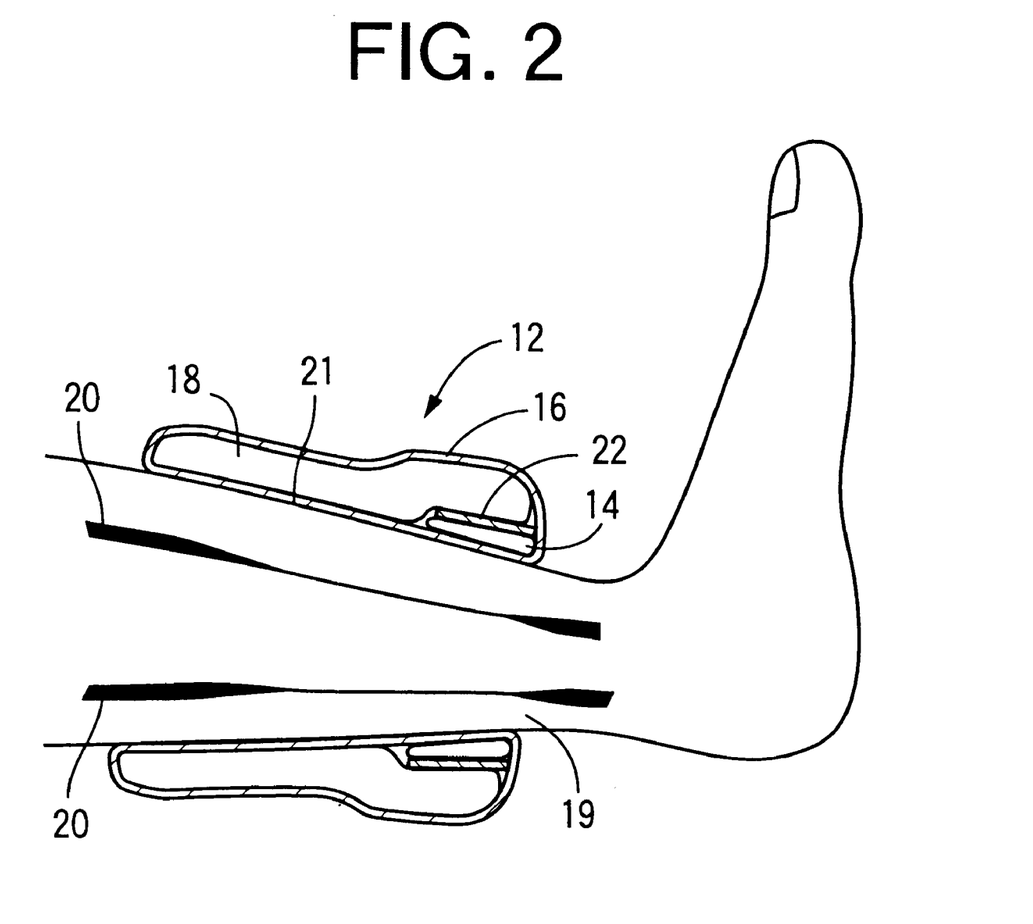
FIG. 2 is a view showing a state in which an inflatable cuff of the apparatus of FIG. 1 is wound around an ankle of a living subject and an artery of the ankle is occluded by the cuff.

FIG. 2 shows a state in which the cuff 12 constructed as described above is wound around the ankle 19 of the living subject and the artery 20 of the ankle 19 is occluded. When the pressing pressure of the cuff 12 is lowered and the pulsation of the artery 20 is allowed, a pressure pulse wave is produced by the pulsation of the artery 20 and is propagated via a body surface 21 to each of the first and second rubber bags 18, 14, so that a pressure oscillation is produced in each of the two rubber bags 18, 14. In addition, as shown in FIG. 2, there is provided a shield plate 22 between the first rubber bag 18 and the second rubber bag 14. The shield plate 22 is provided for preventing the oscillation produced in the first rubber bag 18, from being transmitted to the second rubber bag 14. To this end, the shield plate 22 has prescribed width and length substantially equal to those of the second bag 14, and is formed of a considerably hard, flexible material having a thickness of about 0.3 mm. In FIG. 1, the shield plate 22 is not shown.

The first rubber bag 18 is connected via a piping 23 to a switch valve 24 and a first pressure sensor 25, and the switch valve 24 is connected via a piping 26 to an air pump 28. The second rubber bag 14 is connected via a branch piping 30 of the main piping 23 to a second pressure sensor 32 and the switch valve 24. The diameter of the branch piping 30 connected to the second bag 14 is smaller than that of the main piping 23 connected to the first bag 18. Thus, the branch piping 30 functions as a restrictor device.

The switch valve 24 is selectively placed in one of the following three positions: the first position is a pressure-supply position in which the valve 24 permits pressurized air to be supplied from the air pump 28 to the cuff 12 (i.e., the first and second rubber bags 18, 14); the second position is a slow-deflation position in which the valve 24 permits the pressurized air to be slowly deflated from the cuff 12; and the third position is a quick-deflation position in which the valve 24 permits the pressurized air to be quickly deflated from the cuff 12.

The first pressure sensor 25 detects a first pressure $P_1$ in the first rubber bag 18, and supplies a first pressure signal $SP_1$ representing the detected first pressure $P_1$, to each of a static-pressure filter circuit 34 and a pulse-wave filter circuit 36. The static-pressure filter circuit 34 includes a low-pass filter which extracts, from the first pressure signal $SP_1$, a cuff pressure signal $SK_1$ representing a cuff pressure $PK_1$ as a constant component of the signal $SP_1$, and supplies the cuff pressure signal $SK_1$ to an electronic control device 40 via an analog-to-digital (A/D) converter 38. The pulse-wave filter circuit 36 includes a band-pass filter which extracts, from the first pressure signal $SP_1$, a first pulse wave signal $SM_1$ representing a first pulse wave $M_1$ as a frequency component of the signal $SP_1$, and supplies the first pulse wave signal $SM_1$ to the control device 40 via an A/D converter 42. The first pulse wave $M_1$ represented by the first pulse wave signal $SM_1$ is a pressure oscillation which is produced in the first rubber bag 18 because the pulsation of the artery 20 under the cuff 12 is transmitted to the first bag 18.

The second pressure sensor 32 detects a second pressure $P_2$ in the second rubber bag 14, and supplies a second pressure signal $SP_2$ representing the detected second pressure $P_2$, to a second pulse-wave filter circuit 44. The second pulse-wave filter circuit 44 has the same construction as that of the first pulse-wave filter circuit 36, and includes a band-pass filter which extracts, from the second pressure signal $SP_2$, a second pulse wave signal $SM_2$ representing a second pulse wave $M_2$ as a frequency component of the signal $SP_2$, and supplies the second pulse wave signal $SM_2$ to the control device 40 via an A/D converter 45. The second pulse wave $M_2$ represented by the second pulse wave signal $SM_2$ is a pressure oscillation which is produced in the second rubber bag 14 because the pulsation of a downstream-side portion of a length of the artery 20 under the cuff 12 is transmitted to the second bag 14. Thus, in the present embodiment, the second rubber bag 14, the second pressure sensor 32, and the second pulse-wave filter circuit 44 cooperate with one another to provide a pulse-wave detecting device 46.

The control device 40 is essentially provided by a so-called microcomputer including a central processing unit (CPU) 47, a read only memory (ROM) 48, a random access memory (RAM) 50, an input-and-output (I/O) port, not shown, etc. The control device 40 or the CPU 47 processes input signals according to control programs pre-stored in the ROM 48, while utilizing a temporary-storage function of the RAM 50, and outputs, via the I/O port, drive signals to the switch valve 24 and the air pump 28 and thereby control the same 24, 26. In addition, the CPU 37 determines a BP value or values of the living subject based on the cuff pressure signal $SK_1$ and the first and second pulse wave signals $SM_1$, $SM_2$ all of which are supplied to the control device 40 while the control device 40 controls the switch valve 24 and the air pump 28. Moreover, the control device 40 controls a display device 52 to display the thus determined BP values of the living subject.

Figure 3:
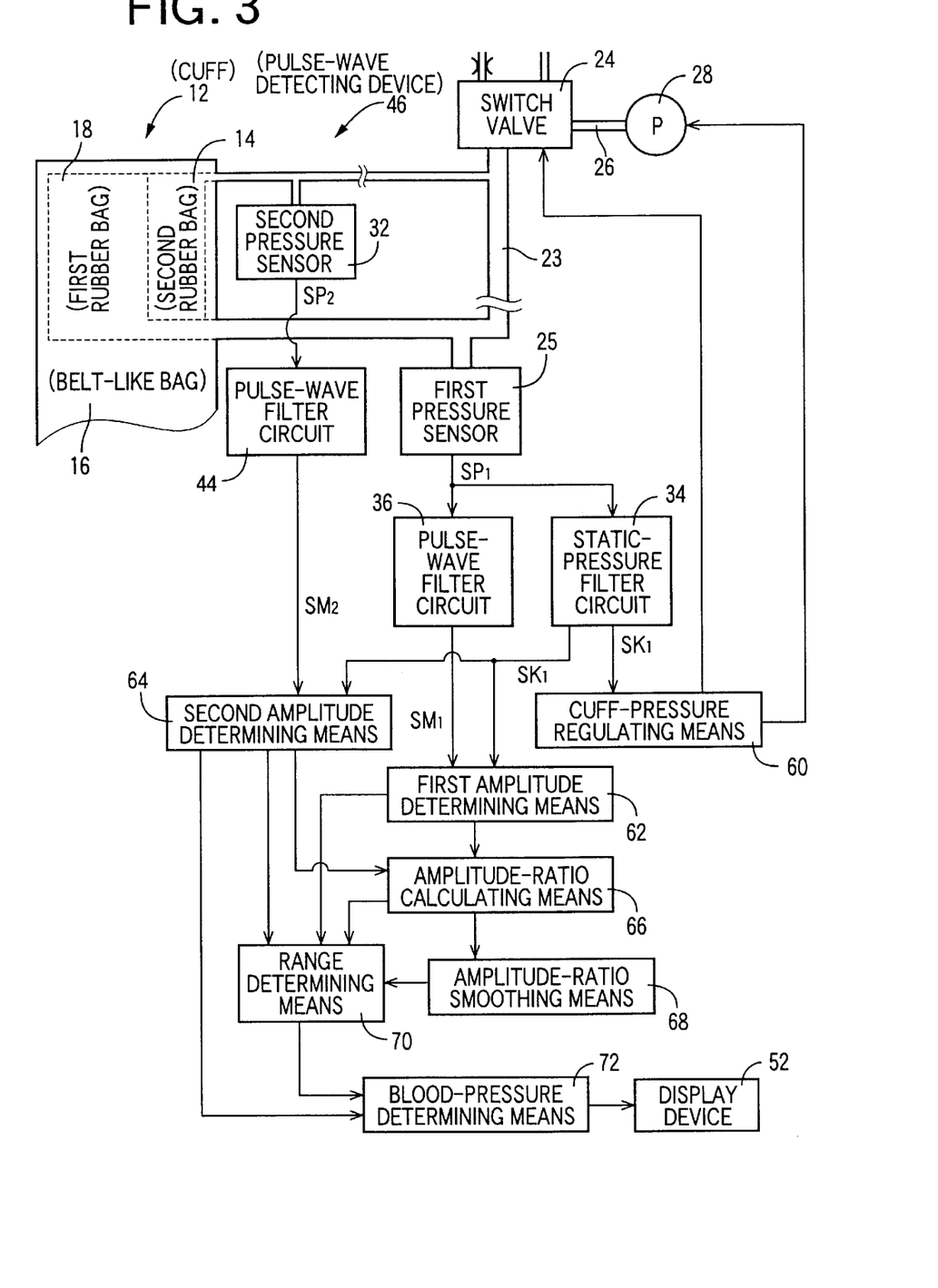
FIG. 3 is a block diagram for explaining essential functions of an electronic control device of the apparatus of FIG. 1.

FIG. 3 is a block diagram for explaining important functions of the control device 40. In the figure, a cuff-pressure regulating means 60 operates the air pump 28 and switches the switch valve 24 to its pressure-supply position, so that the pressure in the cuff 12 wound around the ankle 19 is quickly increased. In addition, when the cuff pressure $PK_1$ in the first inflatable bag 18, detected by the first pressure sensor 25, indicates that the pressure of the cuff 12 has reached a prescribed target pressure value $P_{CM}$ (e.g., about 240 mmHg), the cuff-pressure regulating means 60 switches the switch valve 24 to its slow-deflation position, so that the pressure of the cuff 12 is slowly decreased at a prescribed low rate of about 3 mmHg/sec. And, when the pressure of the cuff 12 becomes equal to a prescribed measurement-end pressure value $P_{CE}$ sufficiently lower than a diastolic BP value $BP_{DIA}$ of the living subject, the cuff-pressure regulating means 60 switches the switch valve 24 to its quick-deflation position, and stops the air pump 28.

A first amplitude determining means 62 determines an amplitude (hereinafter, referred to as the first amplitude $A_1$) of each of heartbeat-synchronous pulses of the first pulse wave signal $SM_1$ which is extracted by the first pulse wave filter circuit 36 from the first pressure signal $SP_1$ produced by the first pressure sensor 25 while the pressure of the cuff 12 is slowly decreased by the cuff-pressure regulating means 62. The first amplitude determining means 62 stores, in a prescribed memory area of the RAM 50, the thus determined first amplitude $A_1$ of each heartbeat-synchronous pulse, together with a cuff pressure value $PK_1$ at the time when the each heartbeat-synchronous pulse is detected by the first pressure sensor 25. The cuff pressure value $PK_1$ is represented by the cuff pressure signal $SK_1$ which is extracted by the static-pressure filter circuit 34 from the first pressure signal SP1.

A second amplitude determining means 64 determines an amplitude (hereinafter, referred to as the second amplitude $A_2$) of each of heartbeat-synchronous pulses of the second pulse wave signal $SM_2$ which is extracted by the second pulse wave filter circuit 44 from the second pressure signal $SP_2$ produced by the second pressure sensor 32 while the pressure of the cuff 12 is slowly decreased by the cuff-pressure regulating means 62. The second amplitude determining means 64 stores, in another prescribed memory area of the RAM 50, the thus determined second amplitude $A_2$ of each heartbeat-synchronous pulse, together with a cuff pressure value $PK_1$ at the time when the each heartbeat-synchronous pulse is detected by the second pressure sensor 25.

An amplitude-ratio calculating means 66 calculates a ratio, r, of one of each first amplitude $A_1$ determined by the first amplitude determining means 62 and a corresponding second amplitude $A_2$ determined by the second amplitude determining means 64 to the other of the each first amplitude $A_1$, and the corresponding second amplitude $A_2$ (i.e., $r=A_1/A_2$ or $A_2/A_1$). Here, it is noted that each first amplitude $A_1$ and a corresponding second amplitude $A_2$ from which a ratio r is calculated are obtained from respective heartbeat-synchronous pulses which are substantially simultaneously produced in the first and second inflatable bags 18, 14 because of a same pulsation of the artery 20 and are substantially simultaneously detected by the first and second pressure sensors 25, 32 from the two bags 18, 14, respectively. That is, each second amplitude $A_2$ used to calculate a ratio r is obtained from a heartbeat-synchronous pulse of the second pulse wave $SM_2$ that is detected at substantially the same time as the time of detection of a heartbeat-synchronous pulse of the first pulse wave $SM_1$ from which a first amplitude $A_1$, used to calculate the ratio r, is obtained.

Though amplitude ratios r may be determined for all the first amplitudes $A_1$ determined by the first amplitude determining means 62 and the corresponding second amplitudes $A_2$ determined by the second amplitude determining means 64, amplitude ratios r, or smoothed amplitude ratios r', described below, may be determined for only a portion of a pre-selected ones of (a) the first amplitudes $A_1$ or (b) the second amplitudes $A_2$ which portion falls within a range which is determined in advance by a range determining means 70, described later.

An amplitude-ratio smoothing means 68 smoothes the amplitude ratios r calculated by the amplitude-ratio calculating means 66, according to a well-known mathematical method, such as median-filter method, moving-average method, or smoothing-differentiation method, and thus provides the smoothed amplitude ratios r'. In the median-filter method, each of the amplitude ratios r which are sequentially calculated is replaced with a median of a predetermined number (e.g., 3 or 5) of amplitude ratios r consisting of the each ratio r and respective same numbers (e.g., 1 or 2) of ratio or ratios r preceding and following the each ratio r. In the smoothing-differentiation method, each of the amplitude ratios r which are sequentially calculated is differentiated by obtaining a linear sum of central differences, according to the following expression (1):

$$y(k) = d/2 \cdot \sum_{n=1}^{N} C_n \{x_{(k+n)} - x_{(k-n)}\} \tag{1}$$

where d is a value determined based on a sampling period T; N is a degree; and C is a coefficient.

For example, $d=1/T$, $N=1$, and $C_1=1$. The expression (1) indicates that the smoothing-differentiation method or process consists of only low-degree adding and subtracting calculations. Since this method has a good nature, it is known as a useful method for processing a signal obtained from a living subject.

Figure 4:
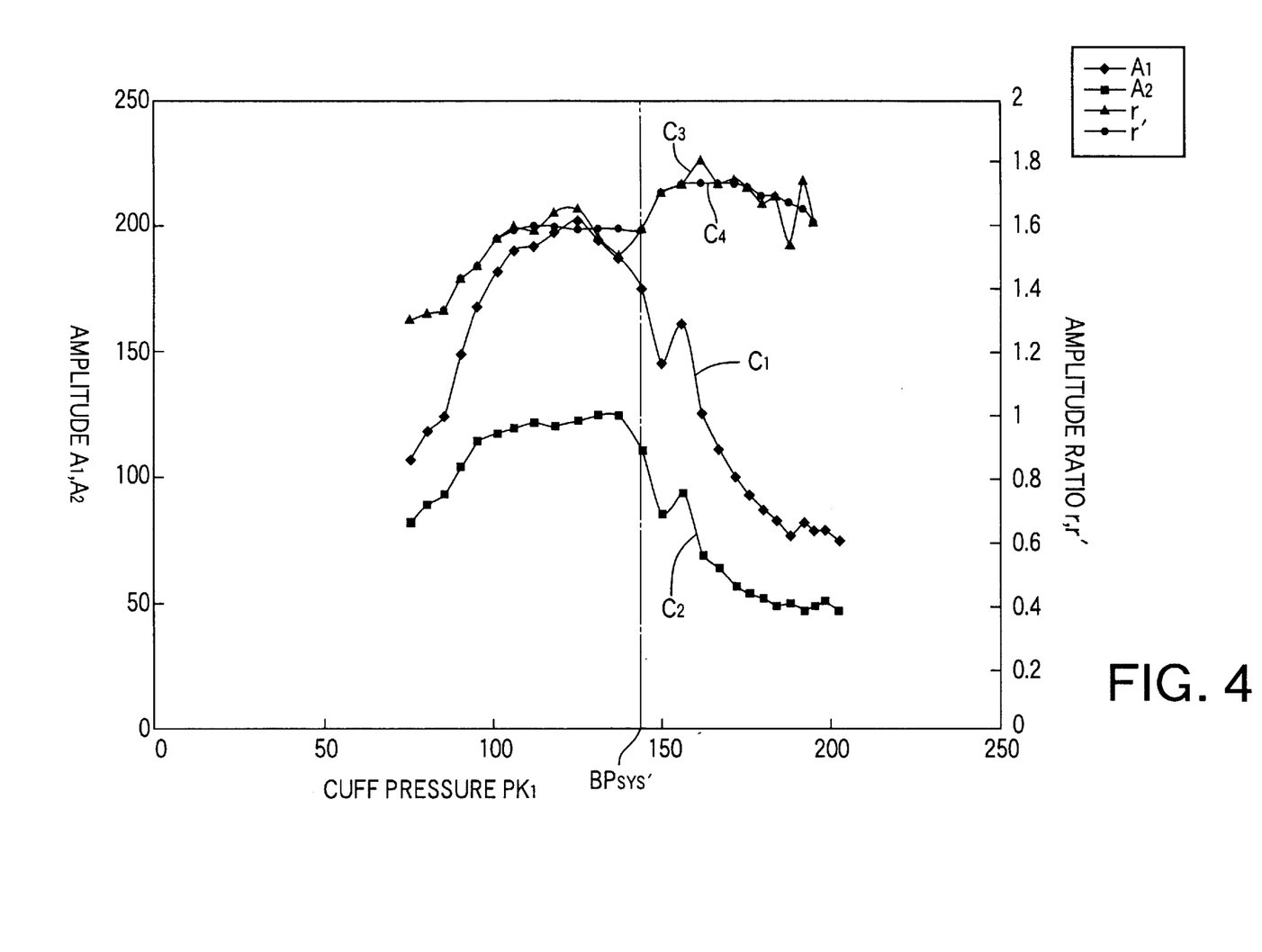
FIG. 4 is a graph showing a curve $C_1$ representing the change of first amplitudes $A_1$, a curve $C_2$ representing the change of second amplitudes $A_2$, a curve $C_3$ representing the change of amplitude ratios r, and a curve $C_4$ representing the change of smoothed amplitude ratios r', all of which are obtained from a normal patient.
Figure 5:
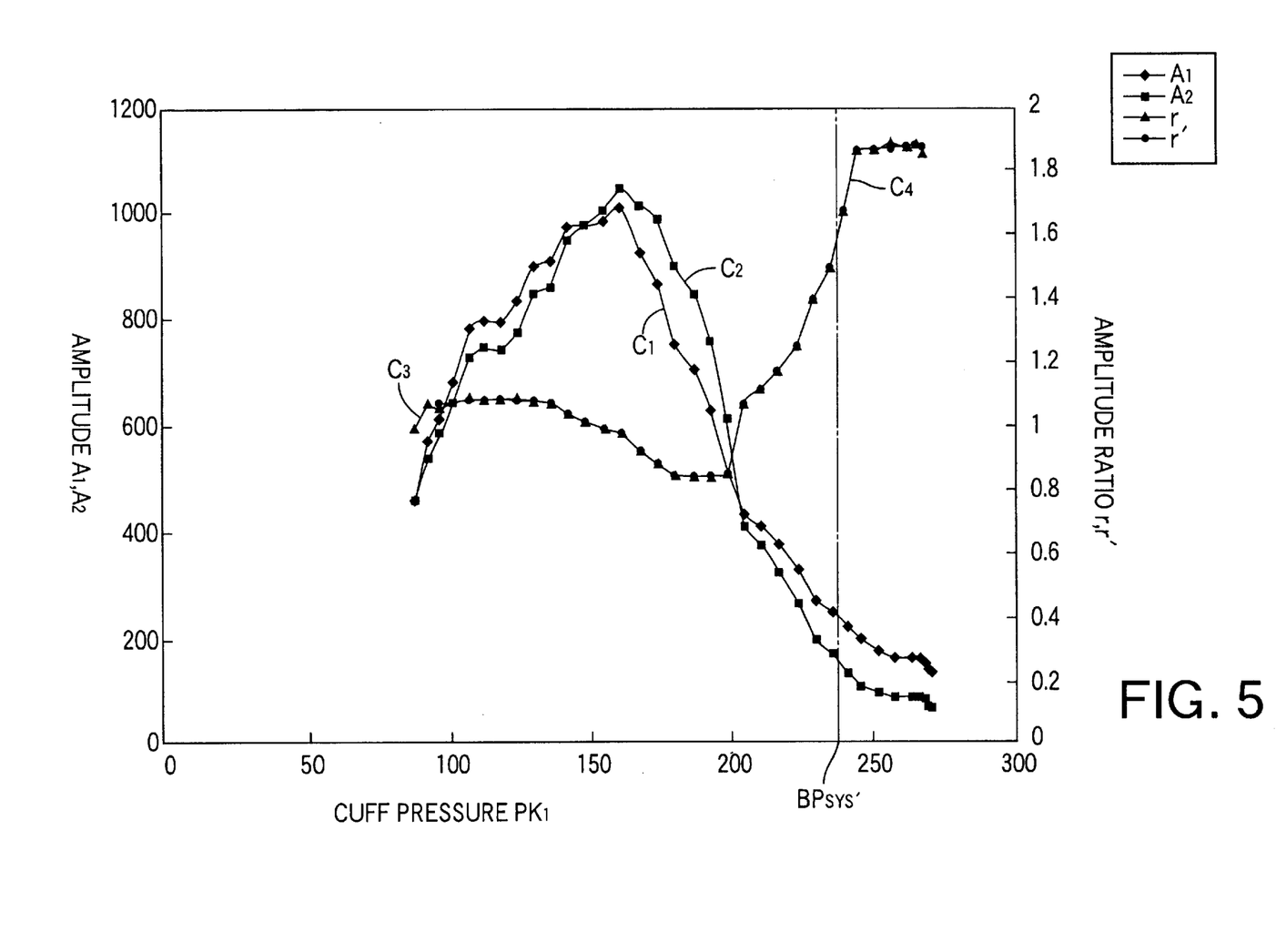
FIG. 5 is a graph showing a curve $C_1$ representing the change of first amplitudes $A_1$, a curve $C_2$ representing the change of second amplitudes $A_2$, a curve $C_3$ representing the change of amplitude ratios r, and a curve $C_4$ representing the change of smoothed amplitude ratios r', all of which are obtained from a hypertension patient.

FIGS. 4 and 5 show respective graphs which are obtained from two different patients. Each of the two graphs is obtained by determining, based on the signals $SK_1$, $SM_1$, $SM_2$ obtained while the pressure of the cuff 12 wound around a corresponding one of the two patients is slowly decreased at the prescribed rate from the prescribed target pressure value $P_{CM}$, first amplitudes $A_1$, second amplitudes $A_2$, amplitude ratios r, and smoothed amplitude ratios r', and plotting the thus determined values $A_1$, $A_2$, r, r' with respect to the cuff pressure $PK_1$. FIG. 4 shows the graph obtained from the first patient whose blood pressure is normal; and FIG. 5 shows the graph obtained from the second patient whose blood pressure is high. In each of the two graphs shown in FIGS. 4 and 5, four curves $C_1$, $C_2$, $C_3$, and $C_4$ represents a relationship between first amplitude $A_1$ and cuff pressure $PK_1$, a relationship between second amplitude $A_1$ and cuff pressure $PK_1$, a relationship between amplitude ratio r and cuff pressure $PK_1$, and a relationship between smoothed amplitude ratio r' and cuff pressure $PK_1$, respectively. Each amplitude ratio r is determined as a ratio of first amplitude $A_1$ to second amplitude $A_2$, i.e., $r=A_1/A_2$. In addition, a BP value $BP_{SYS}'$ is a reference systolic BP value of each patient that is measured by a Doppler's BP measuring method. The Doppler's BP measuring method or apparatus has a disadvantage that it is more difficult for an operator to perform this method or operate this apparatus than perform or operate the oscillometric BP measuring method or apparatus. However, it is known that the Doppler's method measures a reliable systolic BP value from even an ankle of a living subject.

In each of the graphs shown in FIGS. 4 and FIG. 5, the curve $C_1$ representing the change of the first amplitudes $A_1$ or the curve $C_2$ representing the change of the second amplitudes $A_2$ does not have a distinct or clear rising point between the starting point of the slow deflation of the cuff pressure $PK_1$ and respective peak points. Therefore, it is difficult to determine, directly from the curve $C_1$ or the curve $C_2$, a systolic BP value $BP_{SYS}$ according to the oscillometric method. The reason why the curve $C_1$ or the curve $C_2$ does not have a clear rising point can be thought as follows: If the artery 20 of the ankle 19 under the cuff 12 were completely occluded by the cuff 12, the blood would start flowing when the cuff pressure $PK_1$ becomes equal to a systolic BP value $BP_{SYS}$ of the living subject, so that the first amplitudes $A_1$ would abruptly increase. However, the artery 20 of the ankle 19 is one of arteries which cannot be completely occluded by the inflatable cuff 12. Therefore, even if the cuff pressure $PK_1$ may be higher than the systolic BP value $BP_{SYS}$, the pulsation of the artery 20 is transmitted to an upstream-side portion of the cuff 12 wound around the ankle 19, and the amplitude of the pulsation increases as the cuff pressure $PK_1$ decreases. Therefore, the curve $C_1$ does not have a clear rising point where the curve $C_1$ significantly greatly changes to increase. In addition, though the pressure oscillation produced in the first inflatable bag 18 can be shut off by the shield plate 22 to some degree, but cannot be shut off completely. Thus, the pressure oscillation produced in the first inflatable bag 18 is transmitted to the second inflatable bag 14, and accordingly the curve $C_2$ cannot have a clear rising point.

On the other hand, in each of the two graphs, the curve $C_3$ representing the change of the amplitude ratios r and the curve $C_4$ representing the change of the smoothed amplitude ratios r' significantly greatly change around the reference systolic BP value $BP_{SYS}$' measured by the Doppler's method. The reason why the curves $C_1$, $C_2$ do not have a clear rising point but the curve $C_3$ (i.e., the amplitude ratios r) greatly changes around the reference systolic BP value $BP_{SYS}$' can be speculated as follows: As explained previously, while the cuff pressure $PK_1$ is higher than the systolic BP value $BP_{SYS}$, the second rubber bag 14 receives only the attenuated pressure oscillation from the first rubber bag 18. However, when the cuff pressure $PK_1$ becomes lower than the systolic BP value $BP_{SYS}$, the second bag 14 directly receives the pulsation of the artery 20 under the cuff 12. On the other hand, even while the cuff pressure $PK_1$ is higher than the systolic BP value $BP_{SYS}$, the upstream-side portion of the first rubber bag 14 directly receives the pressure oscillation resulting from the pulsation of the artery 20. Therefore, the curve $C_2$ more greatly changes around the systolic BP value $BP_{SYS}$ than the curve $C_1$, and accordingly the amplitude ratios r significantly greatly change around the systolic BP value $BP_{SYS}$.

Meanwhile, in the graph shown in FIG. 4, the curve C3 representing the change of amplitude ratios r temporarily (or shortly) greatly changes at a time immediately after the commencement of the slow deflation of the cuff 12 and at a time when the cuff pressure $PK_1$ is equal to about 160 mmHg. In the case where a systolic BP value $BP_{SYS}$ is determined based on the change of the amplitude ratios r, an erroneous systolic BP value $BP_{SYS}$ may be determined based on each temporary great change of the amplitude ratios r. Hence, the smoothed amplitude ratios r' are obtained by removing or eliminating the temporary great change or changes from the amplitude ratios r.

The range determining means 70 determines a rising range for a pre-selected ones of (a) the first amplitudes $A_1$ or (b) the second amplitudes $A_2$, so that a blood-pressure determining means 72, described below, determines a systolic BP value $BP_{SYS}$ of the subject based on a portion of the amplitude ratios r or the smoothed amplitude ratios r' that are calculated from a portion of the pre-selected first or second amplitudes $A_1$ or $A_2$ that falls within the thus determined rising range. For example, the rising range is defined as a high-pressure range of the cuff pressure $PK_1$ that is higher than a pressure value corresponding to the peak (i.e., maximum value) of the pre-selected first or second amplitudes $A_1$ or $A_2$. FIG. 4 shows that the curve C3 or the curve C4 has a great change in a low-pressure range of the cuff pressure $PK_1$ that is lower than the pressure value corresponding to the peak. However, according to the oscillometric method, a systolic BP value $BP_{SYS}$ should be higher than the cuff pressure value $PK_1$ corresponding to the peak. Therefore, the blood-pressure determining means 72 can determine a systolic BP value $BP_{SYS}$ of the subject based on a portion of the amplitude ratios r or the smoothed amplitude ratios r' that are calculated from a portion of the pre-selected first or second amplitudes $A_1$ or $A_2$ that falls within the thus determined rising range.

The blood-pressure (BP) determining means 72 determines a systolic BP value $BP_{SYS}$ of the ankle 19 of the subject, based on a portion of the amplitude ratios r that are calculated by the amplitude-rate calculating means 66 from a portion of the pre-selected first or second amplitudes $A_1$ or $A_2$ that falls within the rising range determined by the range determining means 70, or based on a portion of the smoothed amplitude ratios r' that are calculated by the amplitude-rate smoothing means 68 from a portion of the pre-selected first or second amplitudes $A_1$ or $A_2$ that falls within the rising range determined by the range determining means 70. As shown in FIGS. 4 and 5, the amplitude ratios r or the smoothed amplitude ratios r' significantly greatly change at the reference systolic BP value $BP_{SYS}$'. For example, the BP determining means 72 calculates a change ratio, d, for each of the above-indicated portion of the smoothed amplitude ratios r' (or of the amplitude ratios r), selects all change ratios d that are greater than a reference change ratio $d_{ST}$, determines one of the thus selected great change ratios d such that the thus determined one great change ratio d corresponds to the highest one of the cuff pressure values $PK_1$ respectively corresponding the selected great change ratios d, and finally determines, as a systolic BP value $BP_{SYS}$ of the subject, the highest cuff pressure $PK_1$ corresponding to the thus selected one change ratio d. In addition, the BP determining means 72 determines, according to the common oscillometric method, a mean BP value $BP_{MEAN}$ and a diastolic BP value $BP_{DIA}$, based on the first amplitudes $A_1$ determined by the first amplitude determining means 62 or the second amplitudes $A_2$ determined by the second amplitude determining means 64. The display device 52 displays the thus determined systolic, mean, and diastolic BP values $BP_{SYS}$, $BP_{MEAN}$, and $BP_{DIA}$.

Figure 6:
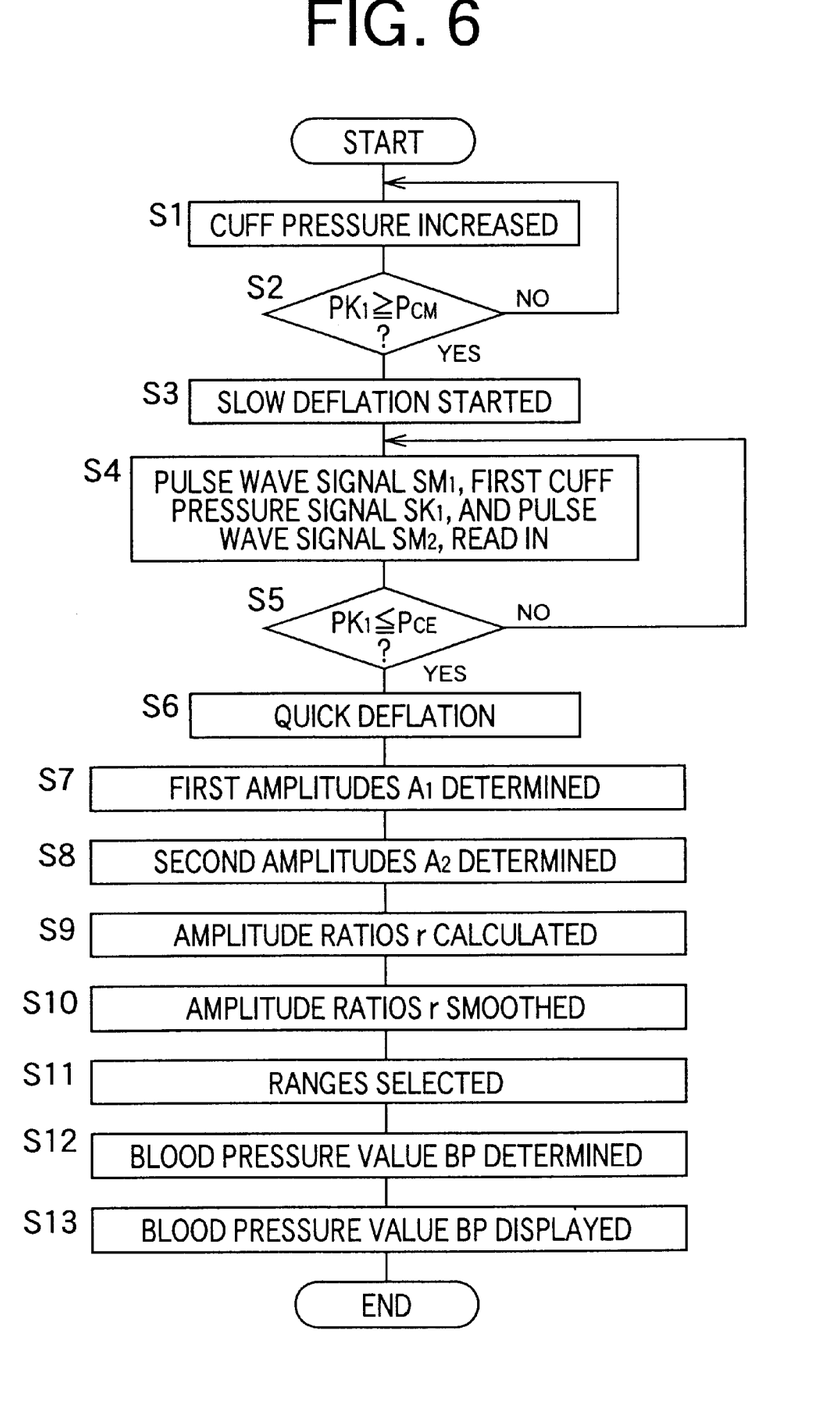
FIG. 6 is a flow chart representing a control program according to which the control device of FIG. 3 controls the BP measuring apparatus of FIG. 1.

FIG. 6 is a flow chart representing a control program or routine according to which the control device 40 controls the BP measuring apparatus 10. The control routine shown in FIG. 6 is started upon operation of a measurement start switch, not shown.

First, the control device 40 carries out Steps S1 to S3 corresponding to the cuff-pressure regulating means 60. More specifically described, at Step S1, the air pump 28 is operated and the switch valve 24 is switched to its pressure-supply position, so as to start increasing the pressure of the cuff 12. That is, the control device 40 starts supplying the pressurized air to each of the first and second inflatable bags 18, 14 of the cuff 12.

At Step S2, the control device 40 judges whether the cuff pressure PK1 has reached a prescribed target pressure $P_{CM}$ (e.g., 240 mmHg) as a pressing pressure which can stop the flow of blood in the artery 20 under the cuff 12. If a negative judgment is made at Step S2, Step S1 and S2 are repeated, while the pressure of the cuff 12 is continuously increased.

On the other hand, if a positive judgment is made at Step S2, the control of the control device 40 proceeds with Step S3 to switch the switch valve 24 to its slow-deflation position, so as to slowly decrease the pressure of the cuff 12 at a prescribed rate of 3 mmHg/sec. That is, the control device 40 starts decreasing the first pressure $P_1$ of the first rubber bag 18 and the second pressure $P_2$ of the second rubber bag 14.

Step S3 is followed by Step S4 where the control device 40 reads in the cuff-pressure signal $SK_1$ supplied from the static-pressure filter circuit 34, the first pulse-wave signal $SM_1$ supplied from the first pulse-wave filter circuit 36, and the second pulse-wave signal $SM_2$ supplied from the second pulse-wave filter circuit 44.

Next, the control device 40 carries out Steps S5 and S6 corresponding to the cuff-pressure regulating means 60. First, at Step S5, the control device 40 judges whether the pressure of the cuff 12 has reached a prescribed measurement-end pressure $P_{CE}$ which is sufficiently lower than a diastolic BP value $BP_{DIA}$ of the subject. If a negative judgment is made at Step S5, Step S4 and S5 are repeated, while the control device 40 continues reading in the cuff-pressure signal $SK_1$ and the first and second pulse-wave signals $SM_1$, $SM_2$. On the other hand, if a positive judgment is made at Step S5, the control goes to Step S6 to switch the switch valve 24 to its quick-deflation position and thereby quickly decrease the pressure of the cuff 12.

At Step S7 corresponding to the first amplitude determining means 62, the control device 40 determines a first amplitude $A_1$ of each of successive heartbeat-synchronous pulses of the first pulse wave $M_1$ represented by the first pulse-wave signal $SM_1$ read in at Step S4, and stores, in a prescribed memory area of the RAM 50, the thus determined first amplitude $A_1$ of the each heartbeat-synchronous pulse, with a cuff-pressure value $PK_1$ at the time of occurrence of the each heartbeat-synchronous pulse having the determined first amplitude $A_1$. An amplitude of each pulse is defined as the difference between a maximum magnitude and a minimum magnitude of the each pulse.

At Step S8 corresponding to the second amplitude determining means 64, the control device 40 determines a second amplitude $A_2$ of each of successive heartbeat-synchronous pulses of the second pulse wave $M_2$ represented by the second pulse-wave signal $SM_2$ read in at Step S4, and stores, in another prescribed memory area of the RAM 50, the thus determined second amplitude $A_2$ of the each heartbeat-synchronous pulse, with a cuff-pressure value $PK_1$ at the time of occurrence of the each heartbeat-synchronous pulse having the determined second amplitude $A_2$.

At Step S9 corresponding to the amplitude-ratio calculating means 66, the control device 40 calculates a ratio r of the first amplitude of each of the successive pulses of the first pulse wave $M_1$, to the second amplitude of a corresponding one of the successive pulses of the second pulse wave $M_2$, i.e., $r=A_1/A_2$, as illustrated in FIGS. 4 and 5.

At Step S10 corresponding to the amplitude-ratio smoothing means 68, the control device 40 smoothes, according to the above-described median-filter method, the amplitude ratios r calculated at Step S9, and provides the smoothed amplitude ratios r', as illustrated in FIGS. 4 and 5.

At Step S11 corresponding to the range determining means 70, the control device 40 determines a peak (i.e., maximum value) of the curve $C_1$, i.e., the greatest one of the first amplitudes $A_1$ determined at Step S7, determines a rising range which is higher than a cuff pressure $PK_1$ at the time of occurrence of the greatest first amplitude $A_1$, and selects the smoothed amplitude ratios r' obtained from the heartbeat-synchronous pulses of the first and second pulse waves $M_1$, $M_2$ that occurred while the cuff pressure $PK_1$ decreased in the rising range.

At Step S12 corresponding to the BP determining means 72, the control device 40 determines a systolic BP value $BP_{SYS}$ of the subject based on the smoothed amplitude ratios r' selected at Step S11. For example, the control device 40 calculates a change ratio, d, of each ($r_1'$) of the selected smoothed amplitude ratio r', to the following selected smoothed amplitude ratio r' ($r_2'$), i.e., $d=r_1'/r_2'$, selects one or more change ratios d greater than a reference change ratio, $d_{ST}$, determines one of the thus selected great change ratios d such that the thus determined one great change ratio d corresponds to the highest one of the cuff pressure values $PK_1$ respectively corresponding to the selected great change ratios d, and finally determines, as a systolic BP value $BP_{SYS}$ of the subject, the highest cuff pressure $PK_1$ corresponding to the determined one great change ratio d. In addition, the control device 40 determines, according to the common oscillometric method, a mean BP value $BP_{MEAN}$ and a diastolic BP value $BP_{DIA}$, based on the first amplitudes $A_1$ determined at Step S7 or the second amplitudes $A_2$ determined at Step S8.

At Step S13, the control device 40 operates the display device 52 to display the systolic, mean, and diastolic BP values $BP_{SYS}$, $BP_{MEAN}$, and $BP_{DIA}$ determined at Step S12. Thus, the present control routine is finished.

In the illustrated embodiment, the first amplitude determining means 62 (Step S7) determines the respective first amplitudes $A_1$ of successive heartbeat-synchronous pulses of the first pulse wave $M_1$ which is produced in the first rubber bag 18 while the pressure of the first bag 18 is slowly decreased; the second amplitude determining means 64 (Step S8) determines the respective second amplitudes $A_2$ of successive heartbeat-synchronous pulses of the second pulse wave $M_2$ which is produced in the second rubber bag 14 while the pressure of the first rubber bag 18 is slowly decreased; the amplitude-ratio calculating means 66 (Step S9) calculates the respective ratios r of the first amplitudes $A_1$ to the second amplitudes $A_2$; and the BP determining means 72 (Step S12) determines the systolic BP value $BP_{SYS}$ of the subject based on the amplitude ratios r. Since the amplitude ratios r significantly greatly changes at the systolic BP value $BP_{SYS}$, the BP determining means 72 (Step S12) can determines the systolic BP value $BP_{SYS}$, based on the amplitude ratios r. Thus, the present BP measuring apparatus 10 can obtain an accurate systolic BP value $BP_{SYS}$ of the subject.

In addition, in the illustrated embodiment, the pulse-wave detecting device 46 includes the second rubber bag 14 which is provided inside, and downstream of, the first rubber bag 18 and whose width is smaller than that of the first bag 18, and detects the pulse wave which is produced in the second bag 14. Thus, the BP measuring apparatus 10 can enjoy a simple construction, and can be produced with ease and at low cost.

In addition, in the illustrated embodiment, the range determining means 70 (Step S11) determines, in advance, the rising range of the cuff pressure $PK_1$, so that a portion (i.e., not all the first or second amplitudes $A_1$, $A_2$) of pre-selected ones of the first amplitudes $A_1$ or the second amplitudes $A_2$ that falls within the determined rising range are used to calculate the amplitude ratios r. Therefore, even if the amplitude ratios r may greatly change in a range different than the rising range, the BP determining means 72 does not erroneously determine a systolic BP value $BP_{SYS}$ in the different range. In addition, even if the amplitude ratios r may temporarily greatly change in the rising range, the amplitude-ratio smoothing means 68 (Step S10) smoothes or eliminates the temporary great change of the amplitude ratios r. Therefore, the BP determining means 72 does not determine an erroneous systolic BP value $BP_{SYS}$, based on the temporary change of the amplitude ratios r that occurred in the rising range. Thus, the present BP measuring apparatus 10 can obtain a more accurate systolic BP value BPsys of the subject.

While the present invention has been described in detail in its preferred embodiment, by reference to the drawings, it is to be understood that the present invention may otherwise be embodied.

For example, in the illustrated embodiment, the control device 40 calculates, at Step S9 of the flow chart of FIG. 6, the respective ratios r of the respective first amplitude $A_1$ of all the successive heartbeat-synchronous pulses of the first pulse wave $M_1$, to the respective second amplitude $A_2$ of all the corresponding heartbeat-synchronous pulses of the second pulse wave $M_2$, subsequently smoothes, at Step S10, all the thus calculated amplitude ratios r, and then selects, at Step S11, a portion of the smoothed amplitude ratios r' that is to be used to determine the systolic BP value $_{SYS}$. However, the control device 40 may be so modified as to calculate respective amplitude ratios r and/or respective smoothed amplitude ratios r' for only a portion of the first or second amplitudes $A_1$ or $A_2$ that falls within the rising range.

In addition, in the illustrated embodiment, the range determining means 70 (Step S11) determines the rising range, so that a portion of the first or second amplitudes $A_1$ or $A_2$ that falls within the thus determined rising range is used by the BP determining means 72 to determine the systolic BP value $BP_{SYS}$. However, the range determining means 70 may be omitted, and the systolic BP value $BP_{SYS}$ may be determined as follows: The BP determining means 72 determines a change ratio d for each of the smoothed amplitude ratios r' (or each of the amplitude ratios r) in an order starting with the highest one of the cuff pressure values $PK_1$ respectively corresponding to the ratios r' (or the ratios r). In this case, the cuff pressure value $PK_1$ corresponding to the smoothed amplitude ratio r' (or the amplitude ratio r) that first exceeds the reference change ratio $d_{ST}$ may be determined as the systolic BP value $BP_{SYS}$. Alternatively, the BP determining means 72 compares each of the smoothed amplitude ratios r' (or each of the amplitude ratios r) with a prescribed threshold value TH in an order starting with the highest one of the cuff pressure values $PK_1$ respectively corresponding to the ratios r' (or the ratios r). In the last case, the cuff pressure value $PK_1$ corresponding to the smoothed amplitude ratio r' (or the amplitude ratio r) that first exceeds the threshold value TH may be determined as the systolic BP value $BP_{SYS}$.

In the illustrated embodiment, the cuff 12 is adapted to be wound around the ankle 19. However, the cuff 12 may be so modified as to be wound around a body portion other than the ankle 19, such as a femoral portion or an upper arm.

In the illustrated embodiment, the lengthwise dimension of the second rubber bag 14 is substantially the same as that of the first rubber bag 18. However, since the second bag 14 is for detecting the pulse wave produced from the artery 20 of the body portion wound which the cuff 12 is wound, the second bag 14 is just required to be located right above the artery 20. Accordingly, the lengthwise dimension of the second bag 14 may be shorter than that of the first bag 18.

In the illustrated embodiment, the BP determining means 72 (Step S12) determines the systolic BP value BPSYS by processing the signals after the slow deflation of the cuff 12 has been finished. However, the BP determining means 72 may be so modified as to determine the systolic BP value BPSYS by processing the signals while the pressure of the cuff 12 is slowly decreased. In the latter case, the pressure of the cuff 12 may be quickly decreased when all the necessary signals have been detected (e.g., when the signal needed to determine the diastolic BP value $BP_{DIA}$ is detected).

In the illustrated embodiment, since the branch piping 30 is thinner than the main piping 23, the piping 30 functions as the restrictor. However, an orifice may be provided in a branch piping 30 whose diameter is equal to that of the main piping 23.

In the illustrated embodiment, the use of the thin piping 30 functioning as the restrictor enables the single air pump 28 and the single switch valve 24 to concurrently regulate the first pressure $P_1$ of the first rubber bag 18 and the second pressure $P_2$ of the second rubber bag 14. However, two air pumps and two switch valves may be employed for the two bags 18, 14, respectively.

In the illustrated embodiment, the second rubber bag 14 is located in the most downstream position of the cuff 12. However, the second bag 14 may be located in a position upstream of the most downstream position, within a downstream-side half portion of the cuff 12.

In the illustrated embodiment, the pulse-wave detecting device 46 includes the second rubber bag 14 provided in the inside and downstream-side portion of the cuff 12, and detects the pulse wave produced in the second bag 14. However, the BP measuring apparatus 10 may employ a different sort of pulse-wave detecting device. For example, it is possible to employ such a pulse-wave detecting device which is provided by (a) a light reflecting plate which is provided, in a substantially middle portion of a cuff, inside the cuff and right above an artery, and (b) an optical distance detector including a light emitting element and a light receiving element which are provided inside the cuff such that those two elements are opposite to the reflecting plate with respect to the artery. Since this pulse-wave detecting device detects a pulse wave by detecting the distance between the reflecting plate and the optical distance sensor that changes because of the pulsation of the artery under the cuff, the pulse wave detected by the pulse-wave detecting device is influenced by the pressure oscillation produced in the first rubber bag 18 as the pressing rubber bag.

It is to be understood that the present invention may be embodied with other changes, improvements and modifications that may occur to one skilled in the art without departing from the spirit and scope of the invention.

What is claimed is:

1. An apparatus for measuring a systolic blood pressure of a living subject, comprising:

an inflatable cuff which is adapted to be wound around a body portion of the subject and includes a first inflatable bag which is inflatable to press an artery of the body portion;

a first amplitude determining means for determining a first amplitude of each of a plurality of heartbeat-synchronous pulses of a first pulse wave which is produced in the first inflatable bag when a pressure in the first bag is changed;

a pulse-wave detecting device which detects a second pulse wave which propagates from the artery to a downstream-side portion of the cuff as seen in a blood-flow direction in which blood flows in the artery;

a second amplitude determining means for determining a second amplitude of each of a plurality of heartbeat-synchronous pulses of the second pulse wave which is detected by the pulse-wave detecting device when the pressure of the first inflatable bag is changed;

a ratio calculating means for calculating a ratio of one of each of the first amplitudes determined by the first amplitude determining means and each of the second amplitudes determined by the second amplitude determining means to the other of said each of the first amplitudes and said each of the second amplitudes; and a blood-pressure determining means for determining the systolic blood pressure of the subject, based on the ratios calculated by the ratio calculating means.

2. An apparatus according to claim 1, wherein the pulse-wave detecting device includes a second inflatable bag which is provided in the downstream-side portion of the cuff wound around the body portion of the living subject, such that the second inflatable bag is located on a downstream side of a first portion of the first inflatable bag and on an inner side of a second portion of the first bag, the second bag having, in the blood-flow direction, a width smaller than a width of the first bag, and wherein the pulse-wave detecting device detects the second pulse wave which is produced in the second bag.

3. An apparatus according to claim 1, wherein the blood-pressure determining means determines the systolic blood pressure of the subject, based on the ratios which are calculated, by the ratio calculating means, based on a portion of pre-selected ones of (a) the first amplitudes or (b) the second amplitudes that falls within a predetermined pressure range.

4. An apparatus according to claim 1, further comprising a smoothing means for smoothing the ratios calculated by the ratio calculating means, wherein the blood-pressure determining means determines the systolic blood pressure of the subject, based on the ratios smoothed by the smoothing means.

5. An apparatus according to claim 4, wherein the smoothing means smoothes the ratios which are calculated, by the ratio calculating means, based on a portion of pre-selected ones of (a) the first amplitudes or (b) the second amplitudes that falls within a predetermined pressure range, and wherein the blood-pressure determining means determines the systolic blood pressure of the subject, based on the ratios smoothed by the smoothing means.

6. An apparatus according to claim 5, wherein the smoothing means smoothes the ratios calculated by the ratio calculating means, according to one selected from the group consisting of a median-filter method, a moving-average method, and a differentiation-smoothing method.

7. An apparatus according to claim 3, further comprising a range determining means for determining, in advance, the pressure range for the pre-selected ones of (a) the first amplitudes or (b) the second amplitudes, wherein the blood-pressure determining means determines the systolic blood pressure of the subject, based on the ratios which are calculated, by the ratio calculating means, based on said portion of the pre-selected ones of (a) the first amplitudes or (b) the second amplitudes that falls within the pressure range determined by the range determining means.

8. An apparatus according to claim 7, further comprising a pressure changing means for increasing the pressure of the first inflatable bag toward a prescribed pressure value, wherein the range determining means determines, for the pre-selected ones of (a) the first amplitudes or (b) the second amplitudes, the pressure range such that the determined pressure range is between the prescribed pressure value and a pressure value of the first bag at a time when a greatest one of the pre-selected ones of (a) the first amplitudes or (b) the second amplitudes occurs.

9. An apparatus according to claim 1, further comprising a pressure changing means for changing the pressure of the first bag.

10. An apparatus according to claim 1, wherein the blood-pressure determining means determines, as the systolic blood pressure of the subject, a pressure value of the first inflatable bag at a time when the ratios calculated by the ratio calculating means significantly greatly changes.

* * * * *